United States Patent [19]
Cundari et al.

[11] Patent Number: 6,063,031
[45] Date of Patent: *May 16, 2000

[54] DIAGNOSIS AND TREATMENT OF TISSUE WITH INSTRUMENTS

[75] Inventors: Michael Anthony Cundari, Hingham; Alan Irving West, Hopkinton; Troy William Roberts, Pepperell; David Raymond Widder, Newton, all of Mass.

[73] Assignee: Assurance Medical, Inc., Hopkinton, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/950,167

[22] Filed: Oct. 14, 1997

[51] Int. Cl.$^7$ ..................................................... A61B 8/00
[52] U.S. Cl. ........................................... 600/439; 600/461
[58] Field of Search .................................. 600/407, 567, 600/561, 587, 437–444, 461, 471, 585

[56] References Cited

U.S. PATENT DOCUMENTS

| | | | |
|---|---|---|---|
| Re. 30,446 | 12/1980 | Meyers et al. | 128/736 |
| Re. 32,000 | 10/1985 | Sagi | 128/736 |
| 3,154,789 | 11/1964 | Lewis, Jr. | 2/104 |
| 3,308,476 | 3/1967 | Kleesattel . | |
| 3,323,352 | 6/1967 | Branson . | |
| 3,744,490 | 7/1973 | Fernandez | 128/2.05 |
| 3,847,139 | 11/1974 | Flam | 128/2 H |
| 3,854,471 | 12/1974 | Wild | 128/2 V |
| 3,880,145 | 4/1975 | Blick | 128/2.05 |
| 3,970,862 | 7/1976 | Edelman et al. | 307/88 ET |
| 3,972,227 | 8/1976 | Tomilov | 73/67.7 |
| 3,996,922 | 12/1976 | Basham | 128/2 R |
| 4,001,951 | 1/1977 | Fasse | 35/17 |
| 4,023,562 | 5/1977 | Hynecek et al. | 128/2.05 E |
| 4,025,165 | 5/1977 | Sollish et al. | 350/161 S |
| 4,132,224 | 1/1979 | Randolph | 128/2 S |
| 4,134,218 | 1/1979 | Adams et al. | 35/17 |
| 4,135,497 | 1/1979 | Meyers et al. | 128/2 H |
| 4,144,877 | 3/1979 | Frei et al. | 128/2 S |

(List continued on next page.)

FOREIGN PATENT DOCUMENTS

| | | |
|---|---|---|
| 2 086 575 | 5/1982 | United Kingdom . |
| PCT/US96/17173 | 10/1996 | WIPO . |

OTHER PUBLICATIONS

Sarvazyan, A. "Knowledge–Based Mechanical Imaging of the Prostate", Medical Technologies & Programs: A Forcast for the future, Aug. 14–17, 1997, pp. 87–94.

Sarvazyan, A., "Knowledge–Based Mechanical Imaging", Tenth IEEE Symposium on Computer–Based Medical Systems, Jun. 11–13, 1997, pp. 120–125.

E.J. Chen et al., "Ultrasound Tissue Displacement Imaging with Application to Breast Cancer", 1995, Ultrasound in Med. & Biol., vol. 21, No. 9, pp. 1153–1156, Michigan, U.S.A.

(List continued on next page.)

*Primary Examiner*—Francis J. Jaworski

[57] ABSTRACT

A device is provided for diagnosis and treatment of tissue with instruments, specifically locating a tissue structure and positioning an instrument relative to that tissue structure. The device which includes a plurality of sensors for generating signals in response to pressure imposed on the sensors as the sensors are pressed against the tissue. The device which includes a member which is configured to be pressed against tissue and the sensors are disposed on the member, for detection of an underlying tissue structure in the tissue. The device also includes a locating device, arranged at a selected position with respect to the sensors, for indicating a location of the underlying tissue structure. An image based on the sensors may be displayed. The method of using the device includes positioning the locating device, which may be an instrument guide, over an underlying tissue structure based on the image. The method further includes using the locating device to direct an instrument for treating or diagnosing a tissue structure towards that tissue structure.

30 Claims, 12 Drawing Sheets

U.S. PATENT DOCUMENTS

| | | | |
|---|---|---|---|
| 4,159,640 | 7/1979 | Leveque et al. | 73/81 |
| 4,190,058 | 2/1980 | Sagi | 128/736 |
| 4,212,306 | 7/1980 | Mahmud | 128/665 |
| 4,219,708 | 8/1980 | Rubey | 200/61.47 |
| 4,250,894 | 2/1981 | Frei et al. | 128/774 |
| 4,286,602 | 9/1981 | Guy | 128/665 |
| 4,291,708 | 9/1981 | Frei et al. | 128/734 |
| 4,346,717 | 8/1982 | Haerten | 600/461 |
| 4,458,694 | 7/1984 | Sollish et al. | 128/734 |
| 4,503,865 | 3/1985 | Shishido | 128/774 |
| 4,524,778 | 6/1985 | Brown, Jr. et al. | 128/736 |
| 4,555,953 | 12/1985 | Dario et al. | 73/862.04 |
| 4,570,638 | 2/1986 | Stoddart et al. | 128/665 |
| 4,600,011 | 7/1986 | Watmough | 128/664 |
| 4,641,659 | 2/1987 | Sepponen | 128/653 |
| 4,641,661 | 2/1987 | Kalarickal | 128/744 |
| 4,651,749 | 3/1987 | Sagi | 128/736 |
| 4,657,021 | 4/1987 | Perry et al. | 128/630 |
| 4,729,378 | 3/1988 | Trittenbass | 128/645 |
| 4,737,109 | 4/1988 | Abramson | 434/267 |
| 4,768,516 | 9/1988 | Stoddart et al. | 128/665 |
| 4,774,961 | 10/1988 | Carr | 128/736 |
| 4,790,329 | 12/1988 | Simon | 128/749 |
| 4,793,354 | 12/1988 | Wright et al. | 128/630 |
| 4,807,637 | 2/1989 | Bjorkhom | 128/664 |
| 4,810,875 | 3/1989 | Wyatt | 250/227 |
| 4,817,623 | 4/1989 | Stoddart et al. | 128/665 |
| 4,873,982 | 10/1989 | Morrison | 128/630 |
| 4,886,070 | 12/1989 | Demarest . | |
| 4,944,298 | 7/1990 | Sholder . | |
| 5,005,581 | 4/1991 | Honeyager | 600/485 X |
| 5,010,772 | 4/1991 | Bourland et al. | 73/862.04 |
| 5,012,817 | 5/1991 | Zeilinski et al. | 128/744 |
| 5,031,634 | 7/1991 | Simon | 128/754 |
| 5,079,698 | 1/1992 | Grenier et al. | 364/413.13 |
| 5,099,848 | 3/1992 | Parker et al. | 128/661.07 |
| 5,140,989 | 8/1992 | Lewis et al. | 128/665 |
| 5,143,079 | 9/1992 | Frei et al. | 128/734 |
| 5,212,637 | 5/1993 | Saxena | 364/413.26 |
| 5,221,269 | 6/1993 | Miller et al. | 604/281 |
| 5,265,612 | 11/1993 | Sarvazyan et al. | 128/660.01 |
| 5,273,046 | 12/1993 | Butterfield et al. | 600/485 |
| 5,301,681 | 4/1994 | DeBan et al. | 128/736 |
| 5,301,682 | 4/1994 | Debbas | 128/737 |
| 5,333,612 | 8/1994 | Wild | 128/660.9 |
| 5,363,852 | 11/1994 | Sharkawy | 600/461 |
| 5,511,561 | 4/1996 | Wanderman et al. . | |
| 5,524,636 | 6/1996 | Sarvazyan et al. | 128/660.9 |
| 5,678,565 | 10/1997 | Sarvazyan . | |
| 5,785,663 | 7/1998 | Sarvazyan | 600/587 |
| 5,795,308 | 8/1998 | Russin | 600/567 |
| 5,807,276 | 9/1998 | Russin | 600/567 |
| 5,833,633 | 11/1998 | Sarvazyan | 600/587 |
| 5,833,634 | 11/1998 | Laird et al. . | |
| 5,836,894 | 11/1998 | Sarvazyan | 600/587 |
| 5,840,023 | 11/1998 | Oraevsky et al. | 600/407 |
| 5,860,934 | 1/1999 | Sarvazyan | 600/587 |

OTHER PUBLICATIONS

R.S. Fearing et al., "A Tactile Sensing Finger Tip for a Dextrous Hand", Oct. 1986, 5th SPIE Intelligent Robotics and Computer Vision, pp. 1–10, Cambridge, Massachusetts.

Brian S. Garra, et al. "Elastography of Breast Lesions: Initial Clinical Results" 1997, Radiology, vol. 202, pp. 69–86.

F. Kallel et al., "Fundamental Limitations on the Contrast–Transfer Efficiency in Elastography: an Analytic Study", 1996, Ultrasound in Med. & Biol., vol. 22, No. 4, pp.463–470.

Dr. Ricki Lewis, "New Imaging Technology May Detect Early Cancer", Biophotonics in Action, Oct. 1996, Photonics Spectra, pp. 52–53.

G. Piperno et al., "Breast Cancer Screening by Impedance Measurements", 1990, Frontiers Med. Biol. Engng. vol. 2, No. 2, pp.111–117.

G.I. Pressman et al., "A Transducer for the Continuous External Measurement of Arterial Blood Pressure", 1960s, IEEE Transactions on Bio–Medical Electronics.

Martin Feder et al., "Transducer Characteristics for Ultrasonic Stereoholography", Dec. 1976, Bull. N.Y. Acad. Med., vol. 52, No. 10, pp. 1207–1223.

B.D. Sollish et al., "Microprocessor–Assisted Screening Techniques", 1981, Israel M. Med. Sci., pp. 859–864, Israel.

R.G. Stevens et al.,"The use of Difference of Gaussian Image Filtering to Assess Objectively the Correlations Between Breast Vascularity and Breast Cancer", 1988, Phys. Med. Biol., vol. 33, No. 12, pp. 1417–1431, U.K.

DIAGNOSIS AND TREATMENT OF TISSUE WITH INSTRUMENTS

BACKGROUND

This application relates to medical diagnosis and treatment of tissue with instruments, specifically locating a tissue structure and positioning an instrument relative to that tissue structure.

Tissue biopsy is an example of treating tissue with medical instruments. One method of performing a biopsy on a suspicious structure in tissue is for a clinician to first palpate the tissue to locate the structure. Upon locating the structure, the clinician uses her fingers to constrain the structure. Once the clinician has done so, the clinician inserts the biopsy needle into the tissue to the approximate depth of the structure. As the needle penetrates the outside portion of the mass, the clinician senses a slight increase in resistance against the needle, which confirms that the needle has reached the structure. Because the clinician does not know for certain the depth of the structure, obtaining a good sample of the tissue or the fluid in the structure typically involves some trial and error. The clinician may insert and reinsert the needle multiple times to ensure that a good sample has been obtained.

Other biopsy methods include stereotactic X-ray imaging, in which two X-ray images at different angles are taken from tissue. The stereotactic image is then used to locate the structure from which the biopsy is to be taken. Ultrasound imaging has also been used to guide the biopsy needle.

SUMMARY

This invention generally concerns diagnosis and treatment of tissue with instruments, specifically locating a tissue structure and positioning an instrument relative to that tissue structure. The invention generally features using a device which includes a plurality of sensors for generating signals in response to pressure imposed on the sensors as the sensors are pressed against the tissue.

In one general aspect, the invention features a device which includes a member which is configured to be pressed against tissue and the sensors are disposed on the member, for detection of an underlying tissue structure in the tissue. The device also includes a locating device, arranged at a selected position with respect to the sensors, for indicating a location of the underlying tissue structure. In another aspect, the invention features a method which includes positioning the locating device relative to the underlying tissue structure based on the signals generated by the sensors.

In another general aspect, a device is provided which includes a member which is configured to be pressed against tissue and the sensors are disposed on the member, for detection of an underlying tissue structure in the tissue. The sensors generate signals in response to pressure imposed thereon by underlying tissue when the member is pressed against the tissue. The device also includes a locating device, arranged at a selected position with respect to the plurality of sensors. A processor generates an image of an underlying tissue structure based on the signals and an indicator of the selected position of the locating device. A display device displays the image and the indicator. In another general aspect, a method of using the device is provided, where the method includes pressing the member against the tissue and positioning the locating device relative to an underlying tissue structure based on the image and the indicator.

In yet another aspect, the invention provides a device which includes a member configured to be pressed against tissue. Sensors disposed on the member generate signals in response to pressure imposed on the sensors by the underlying tissue when the member is pressed against the tissue for detection of an underlying tissue structure in the tissue. A locating device, arranged at a selected position with respect to the sensors, indicates a location of the underlying tissue structure. A constraining device constrains the underlying tissue structure relative to the locating device or the plurality of sensors. In another aspect, a method includes pressing the member against the tissue and constraining the structure relative to the locating device or the plurality of sensors.

Preferred embodiments may include one or more of the following features.

The locating device is an instrument guide for use with an instrument for diagnosing or treating the tissue structure. The instrument guide is configured to be used with a medical instrument which may be one of the following: biopsy instruments, surgical instruments, laser fibers, RF electrodes, cryogenic probes, and devices for implanting materials in the underlying tissue structure. The implanted materials include radioisotopes, drugs, biologic agents, and alcohol. During use, a lubricant may be disposed between the sensor and the tissue.

The locating device includes an instrument guide. The method includes positioning the instrument guide over an underlying tissue structure based on the signals generated by the sensors.

The instrument guide includes a cannula mounted to the member and has a passage which is sized to receive an instrument for treating or diagnosing underlying tissue structures. The sensors are disposed on a lower surface of the member. The cannula is attached to an upper surface of the member. The member includes an opening that is aligned with the passage in the cannula for receiving the instrument. The sensors may be arranged in an array and the opening may be at the center of the array.

A second member is configured to be pressed against tissue. The second member also includes a plurality of sensors disposed on the second member for generating signals in response to pressure imposed on the sensors by underlying tissue when the second member is pressed against the tissue. The instrument guide in this case is arranged at a selected position with respect to the sensors of both members. The members are pivotally mounted with respect to the instrument guide to be pivoted with respect to each other so that an underlying tissue structure is disposed beneath and between the members. The method includes positioning the instrument guide over an underlying tissue structure based on the signals generated by the two pluralities of sensors.

A measurement device determines a pivot angle of one of the members. A processor determines a depth of the underlying tissue structure beneath a surface of the tissue based on the angle and the signals generated by the first mentioned plurality of sensors and the second plurality of sensors. The instrument guide includes a cannula that has a selected length passage sized to receive an instrument for treating and diagnosing underlying tissue structures and the instrument has an adjustable length which allows a user to set the length of the instrument to the selected length of the cannula passage plus the depth of the underlying tissue structure determined by the processor.

The processor generates an image of an underlying tissue structure based on the signals from the sensors. A display displays the image. The processor produces an indicator of the selected position for display on the display device with the image. The processor causes the indicator to be substantially aligned with a portion of the image on the display if a corresponding portion of the underlying tissue structure is positioned beneath the instrument guide.

The method includes manipulating the member on the tissue to cause the image to move with respect to an indicator on the display device until the indicator is substantially aligned with a portion of the image on the display device. The member can be manipulated on the tissue to move the underlying tissue structure. The indicator then indicates that a corresponding portion of the underlying tissue structure is positioned beneath the instrument guide. An instrument for treating and diagnosing underlying tissue structures is inserted through the cannula and opening in the sensors to treat or diagnose the underlying tissue structure when the indicator is substantially aligned with a portion of the image on the display device.

Where there are more than one member, the image may include a first and second image corresponding to the first and second plurality of sensors. In that case, the processor can cause the first image and the second image to be substantially aligned with each other on the display device if the underlying tissue structure is positioned beneath the instrument guide.

The method includes positioning the instrument guide based on the relative positions of the first and second images on the display device. The device is manipulated on the tissue to cause the first image and the second image to move with respect to each other on the display device until portions of the images are substantially aligned on the display device. The alignment indicates that a corresponding portion of the underlying tissue structure is positioned beneath the instrument guide. The members are pivoted with respect to each other so that the underlying tissue structure is disposed beneath and between the members. The length of an instrument for treating or diagnosing underlying tissue structures is adjusted to a selected length which is the length of the cannula passage plus the determined depth of the underlying tissue structure. The guide is then used to direct the instrument to the corresponding portion of the underlying tissue structure that is positioned beneath the instrument guide.

Advantages of the invention may include one or more of the following advantages.

The invention provides visual display of the pressure signals for an underlying tissue structure and information about the depth of a suspicious structure within a tissue. The invention allows guiding the insertion of an instrument for treatment or diagnosis, such as a biopsy needle, into the underlying tissue structure to acquire a sample tissue or aspirate fluids. In some embodiments, the invention allows observing in real time the instruments's movement towards the structure.

In some embodiments, the invention also allows a clinician to target the object of interest accurately and determine a depth quantitatively before the needle is inserted into the tissue. This information reduces the number of erroneous insertions while increasing the likelihood that, for example, a proper tissue or fluid sample from the structure is obtained or the structure is treated properly.

The device can be used with limited training. Therefore, nonspecialist clinicians such as primary care physicians are able to use the device to perform, for example, biopsies.

The invention can be manufactured relatively inexpensively and may be used directly in the office of nonspecialist clinicians.

The device may also be used by the specialists to reduce the number of costly X-ray and ultra-sound procedures, reducing the risk of exposure to and discomfort from these imaging methods.

Other advantages and features will become apparent from the following description and from the claims.

DESCRIPTION

Figure 1:
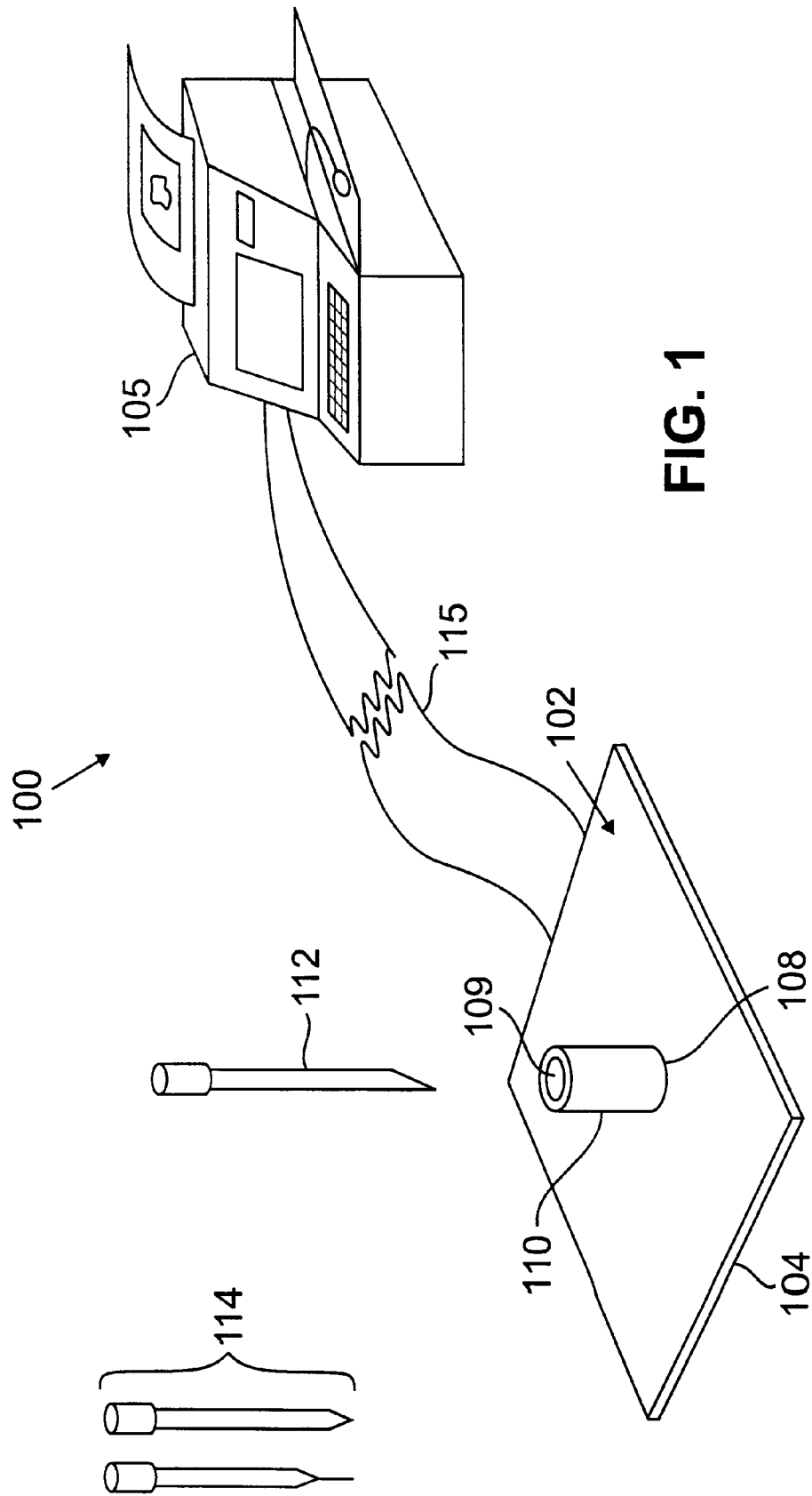
FIGS. 1 and 2 show a first embodiment of an instrument positioning device.
Figure 2:
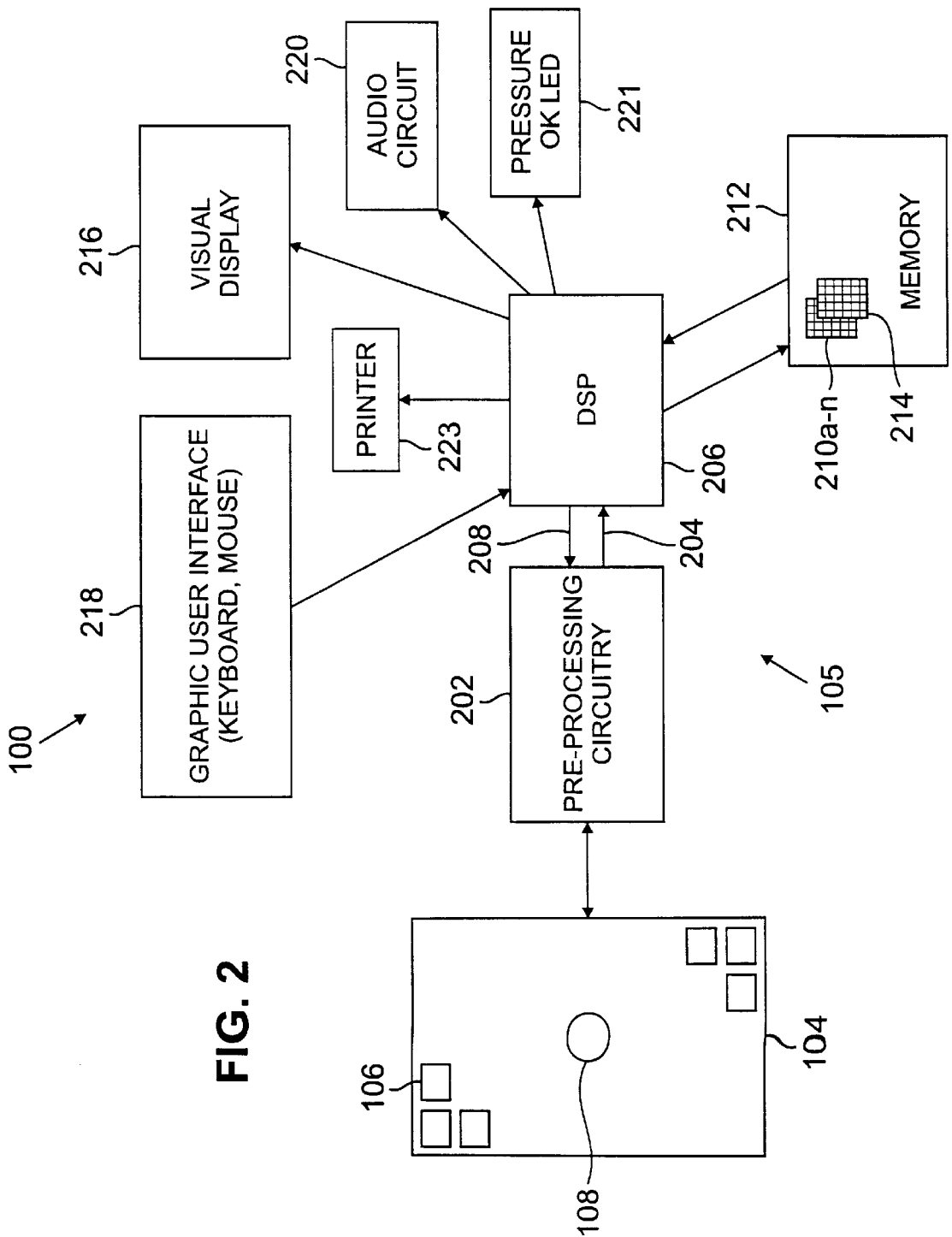

FIGS. 1 and 2 show a first embodiment of an instrument positioning device 100. In the described embodiments herein, we will mainly describe device 100 as it operates a biopsy needle 112. However, device 100 can also operate with other instruments 114 and, for example, guide those instruments towards a tissue structure for diagnosis and treatment of that tissue structure. Examples of instruments 114 include various medical instruments for treatment and diagnosis of tissue including surgical instruments, laser fibers, RF electrodes, cryogenic probes, and devices for implanting materials such as radioisotopes, drugs, biologic agents, and alcohol in the tissue structure.

Instrument positioning device 100 includes a sensor head 102 which includes a thin, flexible membrane and an array 104 of pressure sensors 106 carried on the underside of the membrane. Array 104 is, for example, a contact sensor such as that described in U.S. Pat. No. 4,856,993, entitled "Pressure and Contact Sensor System for Measuring Dental Occlusion" (the '993 patent), incorporated herein by reference, the individual pressure sensors 106 of which are resistive elements. Pressure sensors 106 are arranged in an orthogonal grid of rows and columns in array 104. Pressure sensors 106 are relatively small and are closely spaced to provide high resolution capable of distinguishing between areas of underlying tissue separated by 1 mm or less. Array 104 is commercially available from Tekscan, Inc. (the assignee of the '993 patent).

Sensor head 102 further includes a needle guide cannula 110 arranged at a selected position with respect to sensors 106 (in this embodiment, cannula 110 is centered in array 104). Cannula 110 is rigidly fixed to the upper surface of sensor head 102. A bore 109 through cannula 110 is aligned with a hole 108 in sensor head 102 located at the center of sensor array 104. The cannula operates as an instrument guide. Biopsy needle 112, which may be a needle for fluid aspiration or for core biopsy, slidably fits through cannula 110. As indicated above, biopsy needle 112 is only one example of instruments 114 which may used with instrument positioning device. The use of cannula 110 and biopsy needle 112 is discussed in detail below.

The resistance of each pressure sensor 106 changes in accordance with the amount of pressure applied to sensor 106. The resistance change is inversely proportional to the pressure imposed on sensor 106. Thus, the resistance of each sensor 106 decreases as applied pressure increases.

Device 100 includes a processing subsystem 105 connected to sensor array 104 by a lead 115. Subsystem 105 (which is shown in more detail in FIG. 2) includes preprocessing circuitry 202, which reads the individual resistances of pressure sensors 106 and produces an output 204 that is applied to a digital signal processor (DSP) 206. In other embodiments, DSP 206 may be a microprocessor, or a DSP implemented in software that runs on a microprocessor.

Briefly, preprocessing circuitry 202 sequentially measures the resistance of pressure sensors 106 in response to row and column address signals 208 provided by DSP 206 over lead 115 (FIG. 1) to provide an indication of pressure applied to the location in array 104 that corresponds to that sensor 106. During each resistance measurement, preprocessing circuitry 202 applies a reference potential (not shown) to the addressed sensor 106, measures the voltage drop induced across that sensor 106, and generates an output 204 corresponding to the voltage drop. Thus, each pressure sensor 106 produces a signal (in this example, resistance-induced voltage) in response to the applied pressure. The operation of preprocessing circuitry 202 is more fully described in the '993 patent.

The preprocessor output signals 204 are digitized (by A/D converters, not shown) and applied to DSP 206 on lead 115 (alternatively, an input stage of DSP 206 may perform the A/D conversion). The set of sequentially produced output signals 204 for all pressure sensors 106 in array 104 is termed a "frame." DSP 206 signals preprocessing circuitry 20 to obtain 16 frames per second. DSP 206 stores frames obtained for sensor array 104 in areas 210a–210n of memory 212. Each memory area 210a–210n contains storage locations 214 which respectively correspond to the locations of pressure sensors 106 in a frame. Memory 107 also stores the program logic that runs on DSP 206.

Instrument positioning device 100 includes a visual display device 216 and a keyboard and trackball/mouse combination 218 for inputting data into device 100. Keyboard and trackball/mouse combination 218 allows the clinician to input information such as patient information and also to configure and select various features of instrument positioning device 100.

The operation of the first embodiment of instrument positioning device 100 will now be described in detail in reference to FIGS. 1–6.

Figure 4:
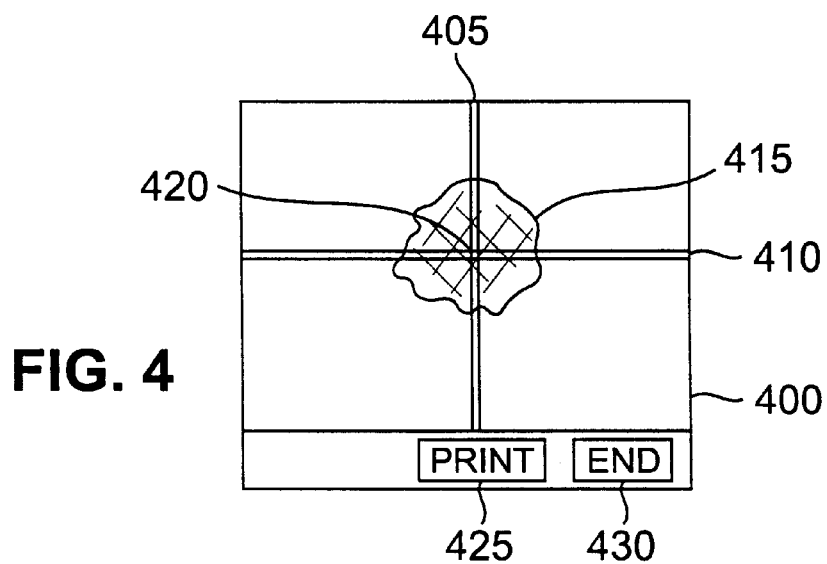
FIGS. 4 and 6 show a user interface displaying images of the pressure signature of a tissue structure.
Figure 6:
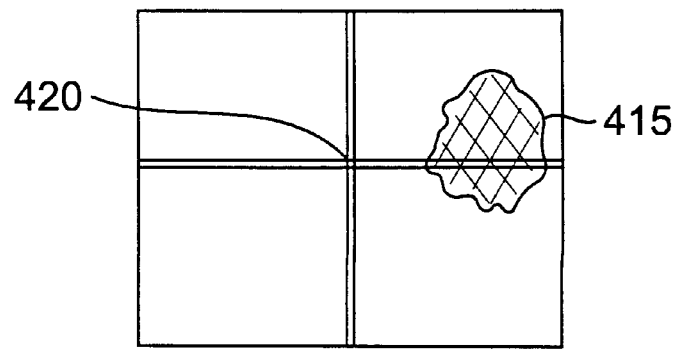

Generally, when instrument positioning device 100 is pressed into contact with the tissue, DSP 206 produces a top view of a three dimensional image generated based on the pressure signals from array 104 for viewing on display device 216. The first two coordinates of the image show the position of the sensors in the array. The third coordinate shows the signal strength output by the sensors. Values on this third coordinate are directly proportional to the stiffness of the underlying tissue and the strength with which the tissue "pushes back" in response to imposed pressure, which will be described in more detail below. FIGS. 4 and 6 illustrate top views of such an image. Because the image is a top view of a three dimensional image, it essentially appears as a two dimensional image with the third dimension being shown by a color scale that correlates to the varying strengths with which the tissue "pushes back" in response to imposed pressure, as will be further described below.

Figure 3:
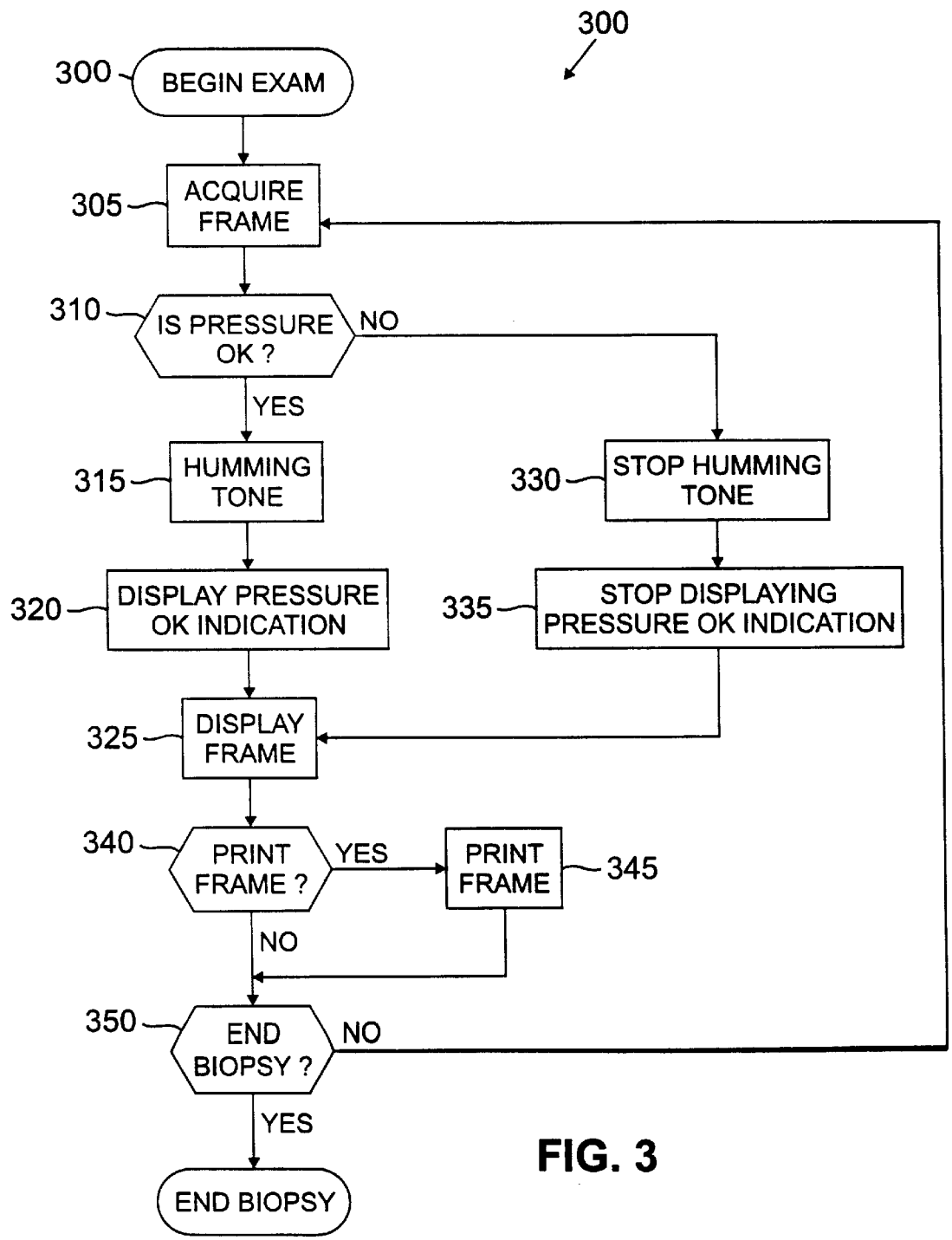
FIG. 3 is a flow chart of the procedure followed by the first embodiment of the instrument positioning device during operation.

FIG. 3 shows a flow chart 300 of the procedure followed by device 100 during operation. Referring also to FIG. 4, when the clinician turns on instrument positioning device 100, DSP 206 drives visual display 216 to display an examination display interface 400. In another embodiment, examination display interface includes a patient data input interface for inputting or changing patient information, including the patient's name, address, identification number and so on. In yet another embodiment, a menu in the input interface permits the clinician to select printing a single frame on a printer, which would provide a record of the structure on which biopsy was performed.

After starting the examination (step 300), clinician translates sensor head 102 across the skin while applying pressure with his hand placed on sensor head 102. DSP 206 signals preprocessing circuit 202 to obtain frames of signals from array 104 (step 305). Because the data from array 104 are sampled data, the data appear to DSP 206, and the clinician, essentially as a series of stationary palpations. At the same time, translating the sensor head allows the clinician to examine more breast area in less time than if the examiner used stationary palpations. Therefore, the clinician is able to more quickly locate the structure on which the clinician would like to perform biopsy.

Generally, the pressure signatures obtained from array 104 are a function of the pressure imposed on sensors 106 by the underlying tissue when the clinician presses array 104 against the body. The resistance of each pressure sensor 106 inversely changes in accordance with the amount of pressure applied to sensor 106. In other words, the resistance of each sensor 106 decreases as applied pressure increases.

The pressure imposed on sensors 106 increases when sensors 106 are pressed against localized areas of stiffer tissue on, within, or below the softer breast tissue. Examples of such stiffer tissue include normal breast tissue structures—such as the nipple, the inframammary ridge, and underlying ribs—and foreign bodies, masses, or structures such as cysts and solid structures (whether or not pathogenic). Consequently, as array 104 is pressed and moved against the breast, the pressure imposed on sensors 106, and thus the resistance of sensors 106, varies in accordance with the properties of the underlying tissue structures.

The pressure applied by the clinician therefore should be within a selected range in order for the pressure signatures to accurately correspond to the various tissue structure types. The limits of the pressure range are a function of size and sensitivity of array 104. For array 104 discussed above, the acceptable pressure range is 0.5 psi to 2.0 psi.

Because the proper amount of clinician-applied pressure is important, a preliminary test 310 is performed on the frame to determine whether the average amount of pressure applied to all sensors 106 is within the acceptable range. Preliminary test 310 also determines if a minimum number of sensors 106 are obtaining a reading across width of array 104 such that DSP 206 recognizes that entire array 104 is in contact with the skin.

If the frame passes initial test 310, DSP 206 triggers audio circuit 220 to produce a low pitched humming tone (step 315) and a "pressure OK" indication, which may be an indication on display device 216 or on another device, such as LED 221 (step 320). DSP 206 maintains the humming tone and "pressure OK" indication throughout the clinical examination to give the clinician feedback that the applied pressure is correct. The pressure signature in a frame is then displayed to the clinician performing the examination (step 325).

If the frame fails test 310 (e.g., if the average applied pressure is below or above the acceptable range), DSP 206 stops the humming tone (step 330) and the "Pressure OK" indication (step 335). The frame is still displayed (step 325) since the clinician may have decreased or increased the pressure on sensor head 102 in order to perform specific kinds of examination for confirming that the correct structure underlies sensor head 102.

DSP 206 processes the frames and displays the results on examination display interface 400 of display device 216 to the clinician. DSP 206 displays a top or plan view of a three dimensional image to the user as part of examination display interface 400. Each image include two axes 405, 410 for permitting signals 204 from individual sensors 106 to be located in the x-y plane. These axes permit the clinician to measure relative size of a structure to assist the clinician in determining whether the structure is the one on which the biopsy is to be performed.

The pressure values from sensors 106 are used to generate the value of the Z-axis for creating the three dimensional image of the pressure signature in a frame. A color pressure scale in the three dimensional image is provided in which ranges of pressure values are defined and each range is assigned a display color. A pressure value which is within a color's range is displayed on visual display 216 with that color. The three dimensional image may also graphically manipulated and displayed in other ways so as to provide further helpful visual cues. For example, various mapping techniques may be used to enhance the top view of the three dimensional image. (As mentioned before, because the image is a top view of the three dimensional image, it essentially appears as a two dimensional image with the third dimension being shown by the color scale.)

In another embodiment, instrument positioning device 100 also displays the image in a perspective view which the clinician may use to confirm the previous diagnosis and determine whether the structure is the same one that was previously selected for biopsy. The device in this alternative embodiment essentially operates as the device disclosed in a commonly assigned patent application entitled "Clinical Tissue Examination", Ser. No. 08/931,573, filed on Sep. 16, 1997, incorporated herein by reference (hereinafter, the '573 application). The perspective view also includes a third axis which represents the pressure detected by sensors 106.

In yet another embodiment, device 100 operates as expert system which analyzes the signals 206 to determine the type of structure, so that the clinician can confirm the previous diagnosis and ensure that the correct structure will undergo biopsy. The device in this alternative embodiment essentially operates as the device in the '573 application and in another commonly assigned patent application entitled "Tissue Examination", Ser. No. 08/757,466, filed on Nov. 27, 1996, incorporated by reference herein (hereinafter, the "466 application").

The clinician at any point can use the user interface 218 to "click" on a print button 425 (FIG. 4) and print a displayed frame on printer 223 (FIG. 2), although the request is not processed until DSP 206 reaches step 340. If the clinician has selected to print a frame (step 340), the image is printed out for placing the image in the patient's file. Similarly, the clinician at any point can "click" on a end button 430 (FIG. 4) to end the examination, although that request is not processed until DSP 206 reaches step 350. If the clinician has selected to end the biopsy (step 340), DSP 206 will end the examination.

When the clinician has located the structure the clinician is to perform biopsy on, the clinician then aligns cannula 110 with the structure such that cannula 110 guides biopsy needle 112 to a desired location in the structure. This desired location is usually the core or the center of the structure. The intersection 420 of axes 405 and 410 indicates the selected position of cannula 110 relative to the array 104 (e.g., the center of sensor array 104, as shown in FIG. 4). Therefore, the clinician aligns intersection 420 with the center of a shape 415 displayed on examination display interface 100, which represents the underlying structure on which the biopsy will be performed. In effect, cannula 110 acts as a locating device for indicating the position of the underlying tissue structure.

Figure 5:
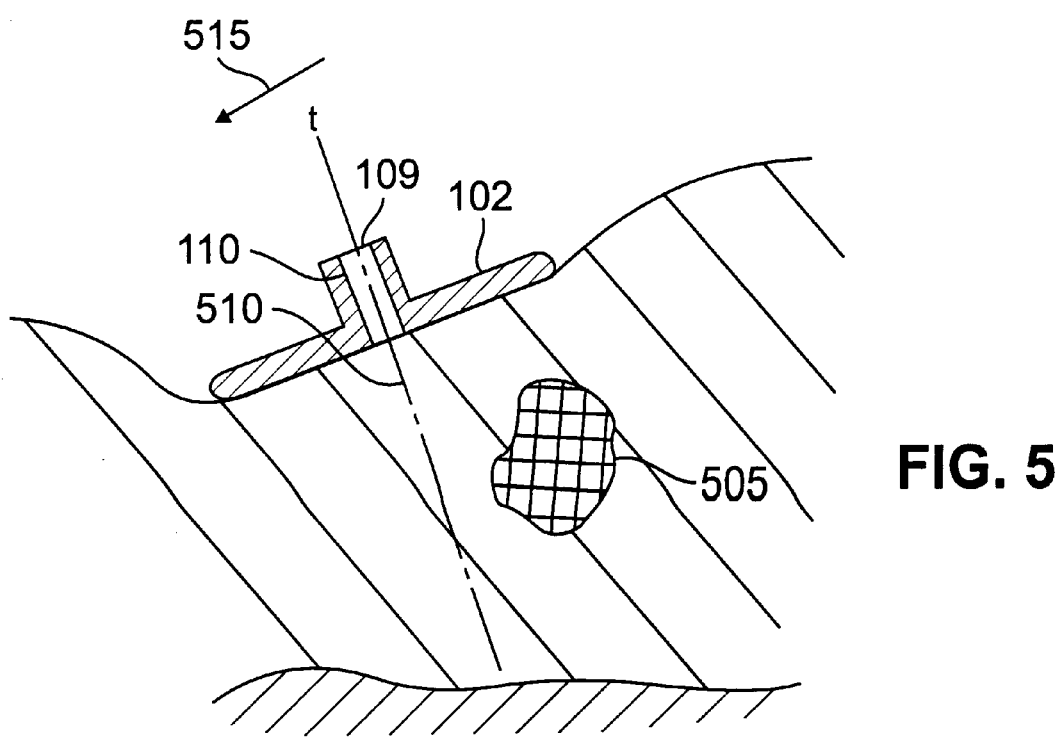
FIGS. 5 and 5A show the relation of a sensor head in the first embodiment of the device to a structure in the tissue.

An incorrect angulation or translation of the device 100 relative to the structure, as shown in FIG. 5, may result in cannula 110 being misaligned relative to underlying structure 505 on which biopsy is to be performed. Therefore, path 510 of biopsy needle 112 (i.e., the axis of cannula bore 109) will not be aligned with the center of structure 505. Consequently, the shape 415 representative of the underlying structure does not appear under intersection 420, as shown in FIG. 6.

If such misalignment occurs, the clinician moves sensor head 102 to align structure 505 with cannula 110, using axes 405, 410. Such movement of sensor head 102 may involve translating sensor head 102 or changing the incident angle of sensor head 102 (e.g. by rotating sensor head 102 in direction 515 in FIG. 5). The movement may also include moving sensor head 102 so as to manipulate the tissue and to move or cause to move the underlying tissue structure relative to the cannula. While manipulating sensor head 102 in this way, the clinician observes how shape 415 moves with respect to axes 405, 410 in the image shown in examination display interface 400. The clinician therefore can dynamically adjust the position of sensor head 102 until the image of shape 415 is aligned with intersection 420.

Figure 5A:
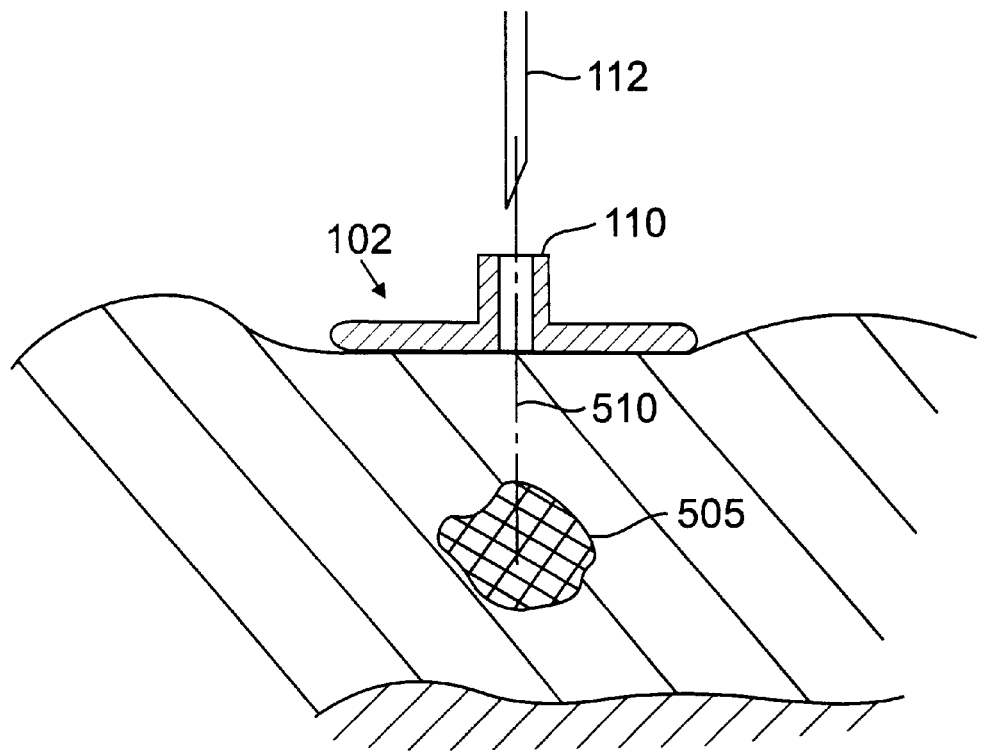

Referring to FIG. 5A, once the image of shape 415 is aligned with intersection 420, clinician can insert biopsy needle 112 into cannula 110 to perform the biopsy. The cannula 110 will guide biopsy needle 112 along path 510 (FIG. 5) towards the center of structure 505. Since inserting the needle into the anatomy may result in the underlying structure moving or changing shape, the clinician can track the insertion of needle 112 in real time by observing the position of image 415 relative to intersection 420, and adjust sensor head 102 as necessary to ensure proper alignment of needle 112 with underlying structure 505. The clinician then confirms that the needle has penetrated the underlying tissue structure by the change in pressure on biopsy needle 112. The clinician then aspirates fluid, or takes a tissue sample, from the structure.

Other embodiments are within the scope of the following claims.

Figure 7:
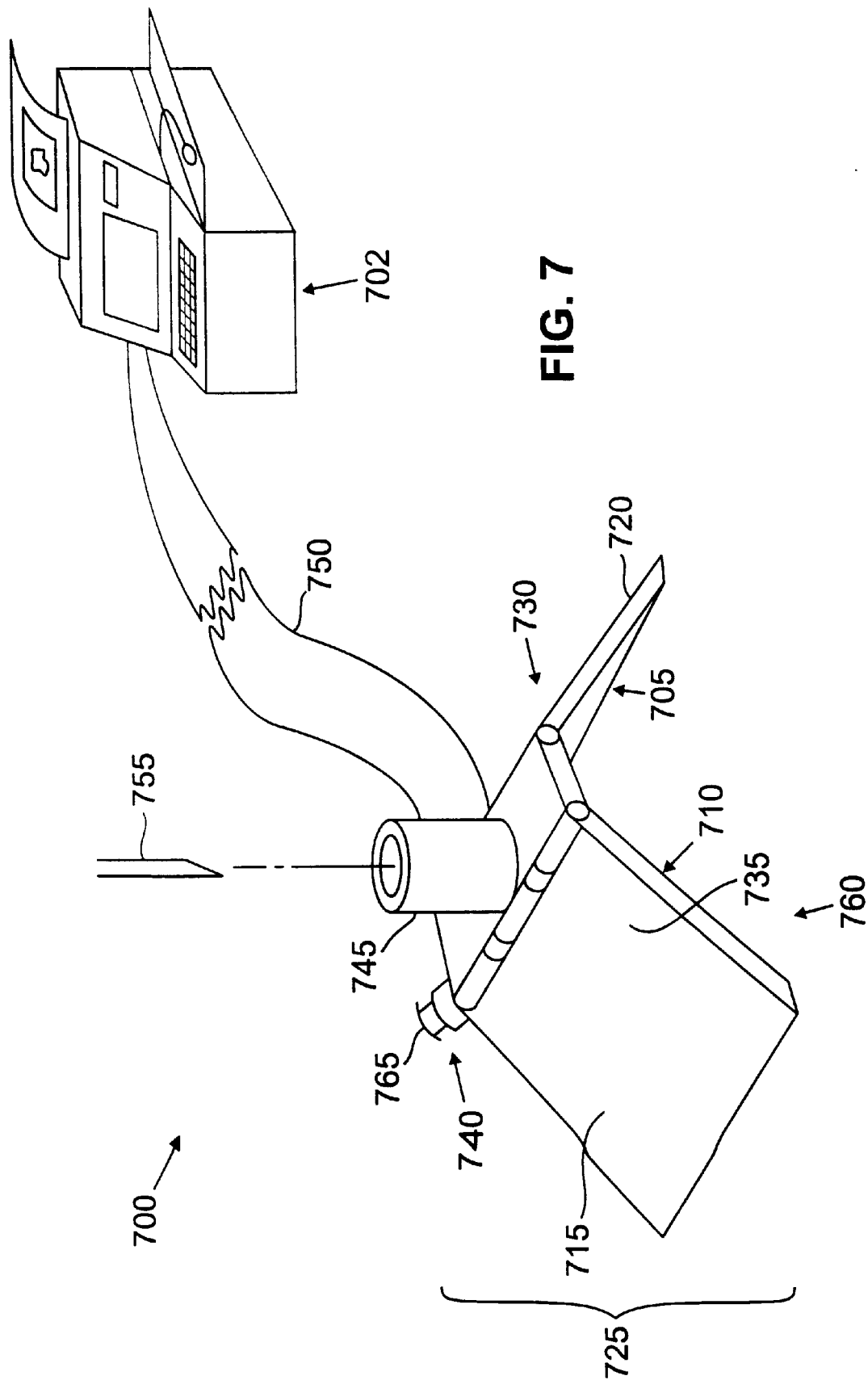
FIGS. 7 and 8 show a second embodiment of an instrument positioning device.
Figure 8:
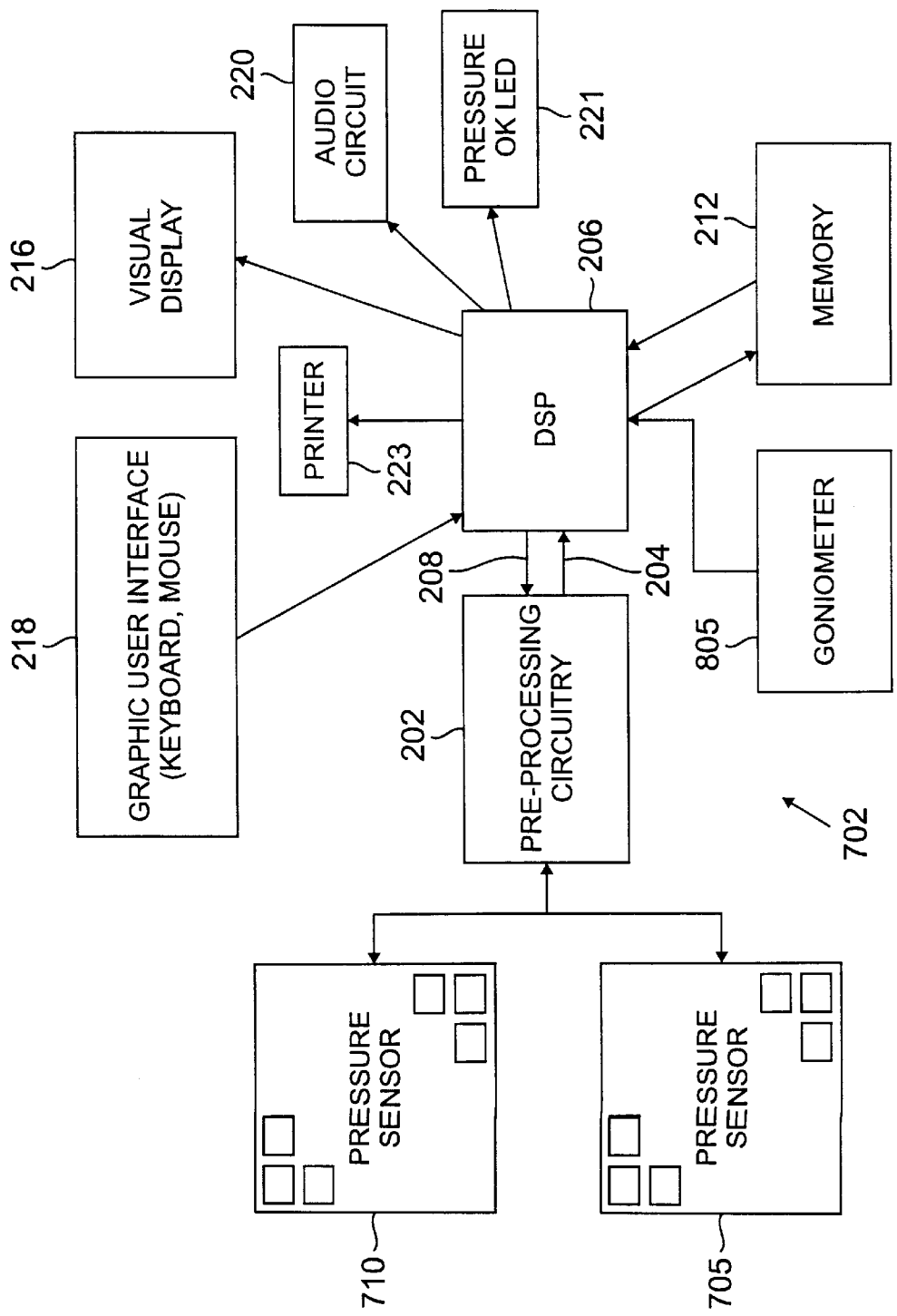

For example, referring to FIGS. 7 and 8, a second embodiment of an instrument positioning device 700 includes a sensor head 760 connected to processing subsystem 702. As in the case of the first described embodiment, we will mainly describe device 700 as it operates with a biopsy needle. However, as in the case of device 100, device 700 can also operate with other instruments 114, for example those described in relation to device 100.

Sensor head 760 includes two sensor arrays 705 and 710. Each one of arrays 705 and 710 is the same as array 104 of device 100. Arrays 705, 710 are installed on the underside of two extensions 715, 720 which form part of a sensor head 725. Extensions 715, 720 are pivotally connected by hinges 730, 735 to a plate 740. A goniometer 805 (or, alternatively an optical encoder) determines the pivot angle 6 of extensions 715, 720 relative to plate 740 (plate 740 is perpendicular to the longitudinal axis of cannula 745). Extensions 715, 720 are constructed to move in unison so that arrays 705 and 710 are each at an angle relative to plate 740 that is equal to the angle of the other array relative to plate 740. Extensions 715, 720 can also be locked at a selected angle by a locking mechanism 765. Cannula 745 is positioned at the center of plate 740 and has the same structure as cannula 110 of instrument positioning device 100. The sensors in arrays 705, 710 are connected to a common lead 750 which transmits signals from the sensors to preprocessing circuit 202.

A biopsy needle 755 slidably fits through cannula 745. As indicated above, biopsy needle 755 is only one example of instruments 114 (shown FIG. 1) which may used with instrument positioning device. Needle 755 may be a needle for fluid aspiration or for core biopsy.

FIG. 8 shows a block diagram of instrument positioning device 700, which is similar to device 100 but includes some additional features. In device 700, preprocessing circuit 202 receives signals from two sensor arrays 705, 710. Moreover, goniometer 805 inputs to DSP 206 the pivot angle θ of the extensions 715, 720 relative to plate 740. This angle is the same as an angle between a line extending perpendicular to each extension 715, 720 and the longitudinal axis of cannula 745 (see FIG. 10).

Device 700 performs two functions which device 100 does not. First, device 700 restricts the mobility of the underlying structure by exerting pressure on the structure from two sides by its extensions 715, 720. Second, in device 700, DSP 206 calculates and displays a depth scale on display 216 based on pivot angle θ, which the clinician uses to determine the depth of the underlying structure, as will be described in detail below.

Figure 9:
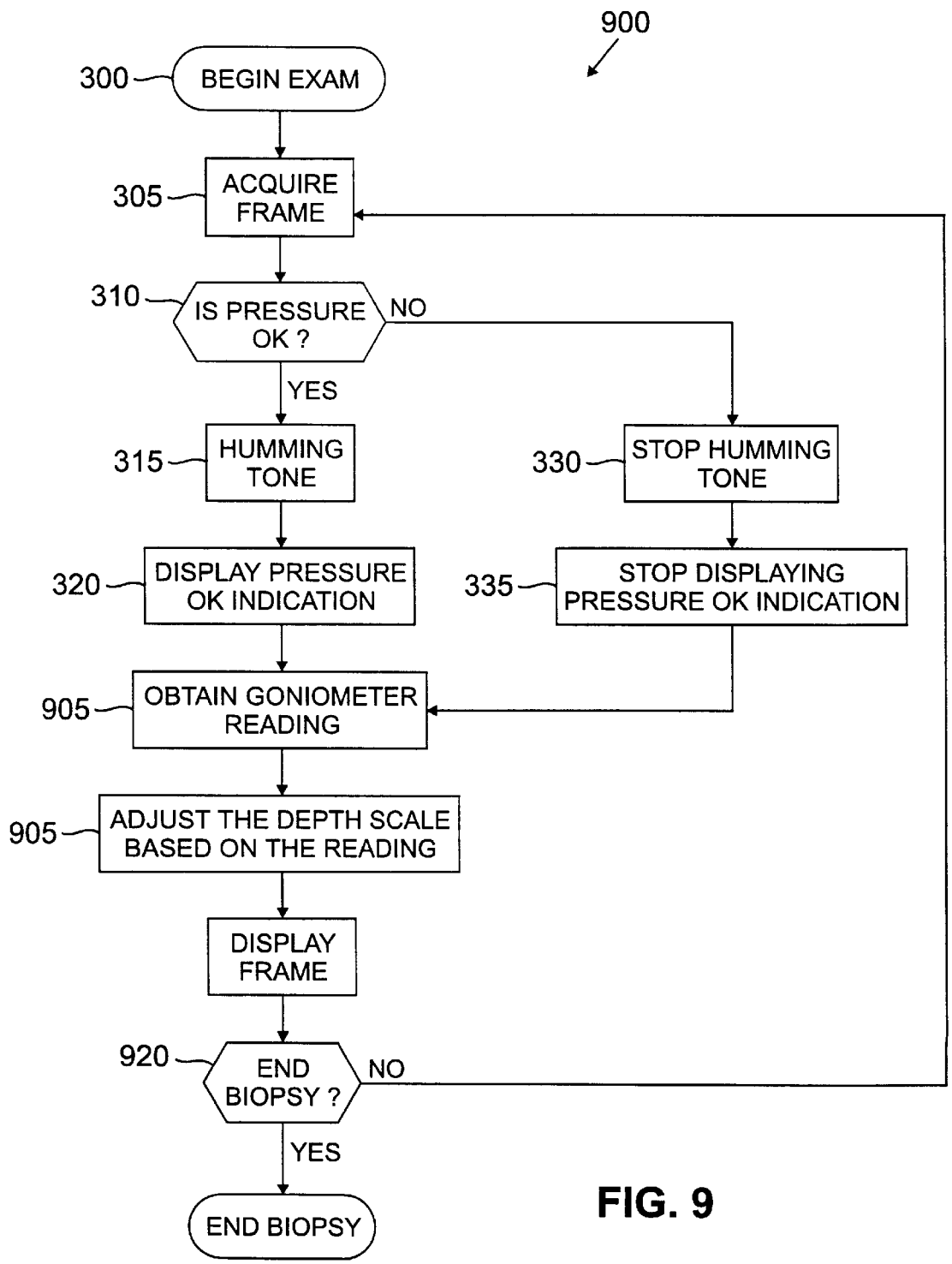
FIG. 9 is a flow chart of the procedure followed by the second embodiment of the instrument positioning device during operation.

FIG. 9 shows a flow chart 900 of the operation of device 700. The steps 300–320 and 330–335 have the same reference numbers as those in flow chart 300 for device 100 (FIG. 3), and are essentially the same, except that pressure signals are obtained from two arrays as opposed to only one array in device 100. The two arrays are connected to common lead 750.

Figure 10:
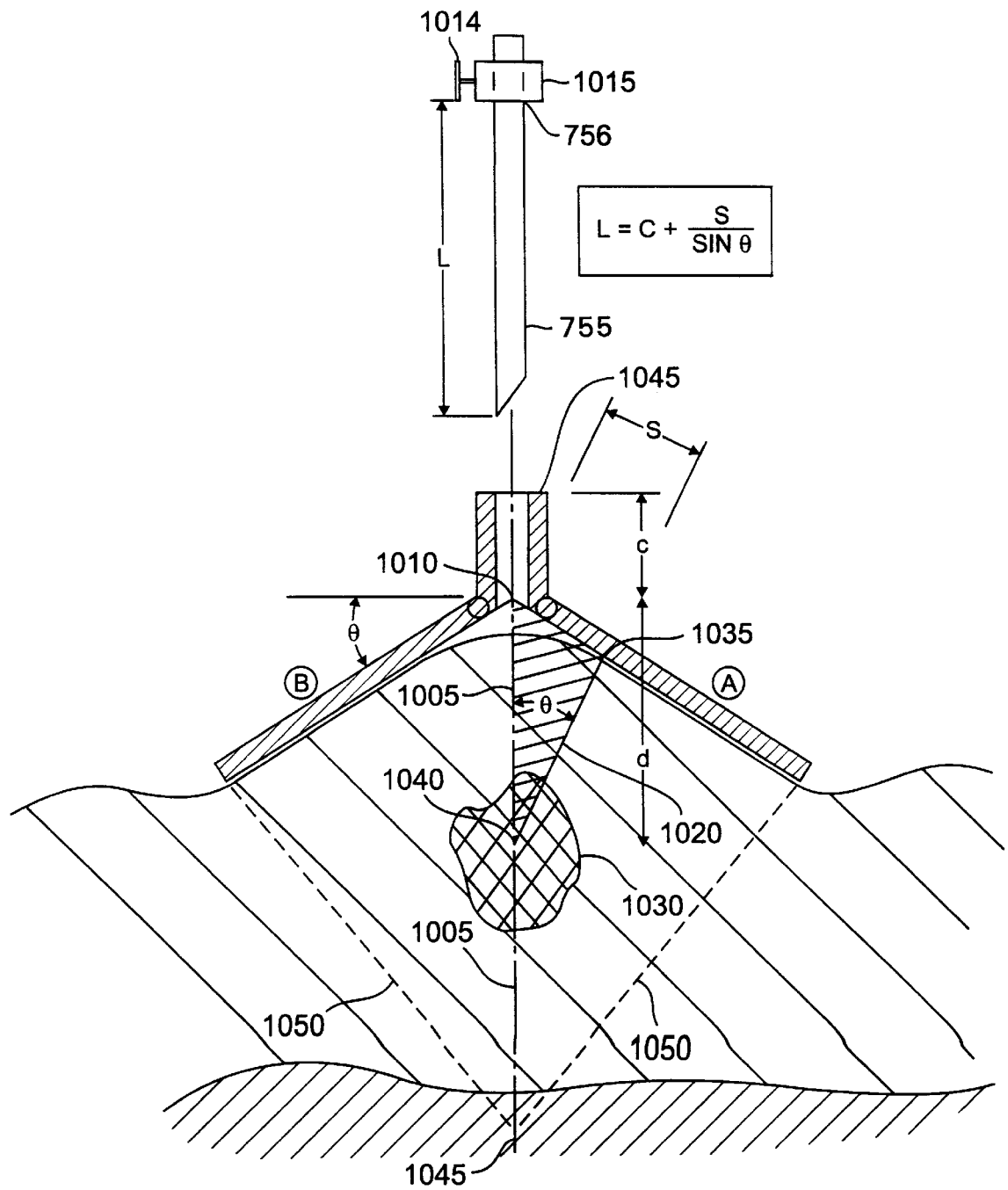
FIGS. 10 and 12 show the relation of a sensor head in the second embodiment of the device to a structure in the tissue.

In step 905, DSP 206 obtains the angle θ of extensions 715, 720 from goniometer 805. In step 910, DSP 206 computes a depth scale for display with signals 204 or display 216. Referring also to FIG. 10, the depth scale shows the depth of a point on path 1005 of biopsy needle 755, based on the position of a given sensor which would read the pressure from that point if any pressure was exerted by that point on that sensor. Since an underlying structure generally applies pressure perpendicular to the surface of an array, the point on path 1005 that would exert pressure on a given sensor is a point at an intersection of a line extending from the sensor perpendicular to the surface of the array (hereinafter, "sensor line") and path 1005. The method of selecting this sensor so that it corresponds to the center of a structure will be described in detail below.

The depth (d) of this point is determined based on the following trigonometric equation:

$$\text{Depth} = \frac{S}{\sin\theta} \quad (1)$$

where θ is the pivot angle between the arrays and plate 740, which is equal to the angle between path 1005 and sensor line 1020; S is the distance of the sensor from a point of intersection 1010 of path 1005 and the line representing the surface of the array. Therefore, the distance from the upper surface 756 of cannula 755 to that point can be determined based on the following equation:

$$L = C + \frac{S}{\sin\theta} \quad (2)$$

where L is the distance from cannula upper surface 756 to point of intersection 1010 and all other variable are the same as equation 1.

In step 910, DSP 206 uses equation (2) and the goniometer reading to calculate the depth scale. The displayed depth scale shows the depth along path 1005 measured from cannula upper surface 756. We will describe in detail below how the clinician uses the depth scale to determine the depth of the center of a structure.

Figure 11:
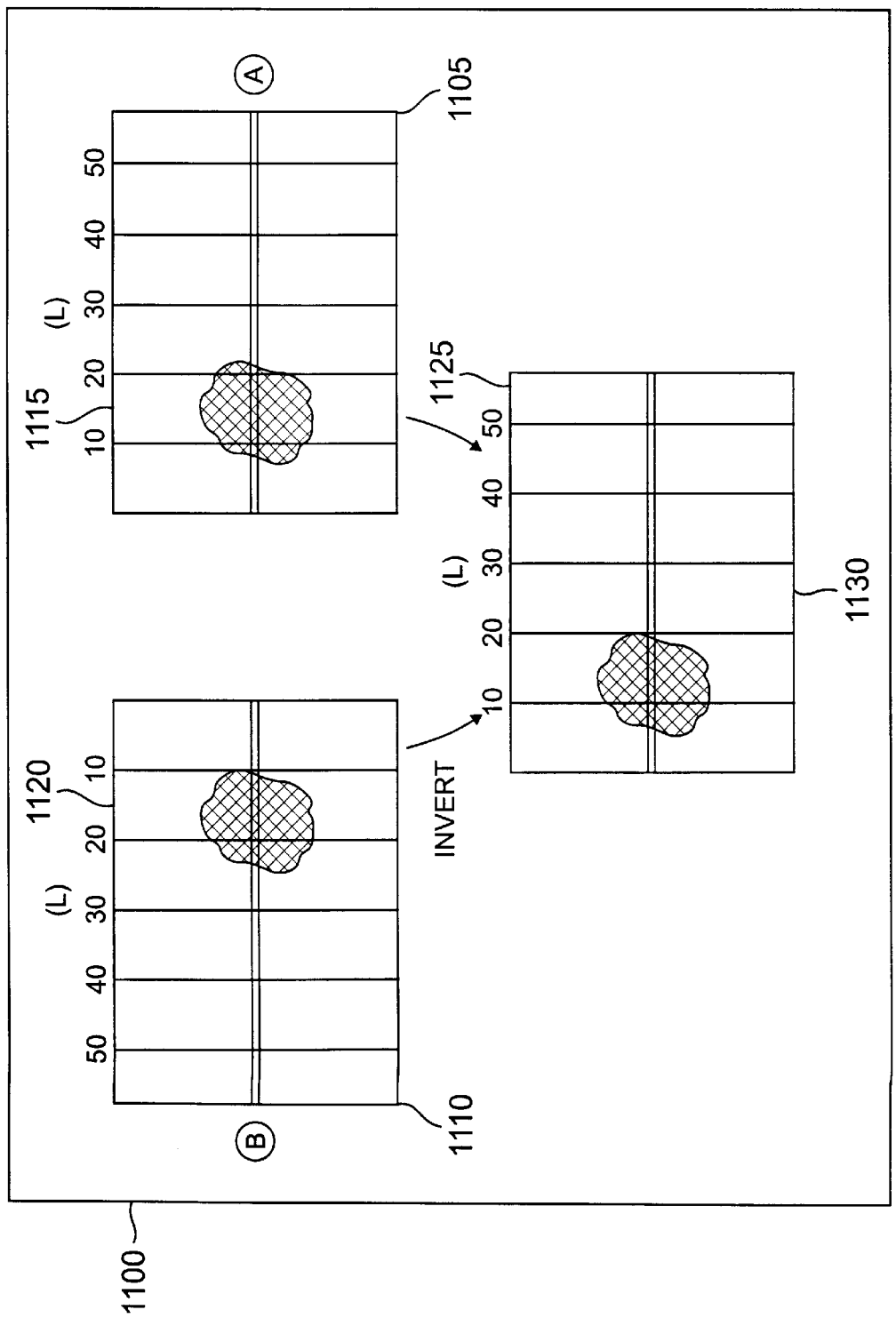
FIGS. 11 and 13 show a user interface displaying images of the pressure signature of a tissue structure.

In step 915, the frames from arrays 705, 710 are displayed together with the depth scale. FIG. 11 shows an examination display interface 1100 for displaying the frames. Image 1105 corresponds to array 705 and image 1110 to array 710. These images have generally the same characteristics as the images in the first embodiment, described above. Image 1130 is a combination of images 1105 and 1110, obtained by flipping image 1110 along its width and superimposing it on image 1105. Image 1130 is used by the clinician to center a suspicious structure along path 1005 of biopsy needle 755, as will be discussed in detail below. Depth scales 1115, 1120, and 1125 are the depth scales calculated and displayed with images 1105, 1110, and 1130.

Following displaying the frames, DSP 206 determines whether the clinician has selected to end the procedure DSP 206 is executing (step 920). If so, DSP 206 ends the procedure. If not, DSP 206 continues to obtain more data from arrays 705, 710.

As mentioned, the clinician uses the depth scale to determine the depth of the center of a structure. To accurately do so, the clinician performs two tasks which we will describe briefly here and in further detail below.

First, the clinician positions sensor head 760 relative to the structure such that the center of the structure is positioned substantially along path 1005. This is necessary because the center of the structure is where the biopsy needle must reach to obtain a good tissue or fluid sample. Moreover, depth scale only shows depths of points on path 1005. Therefore, unless the structure is centered along path 1005, the depth scale does not provide the depth of the center of the structure. To center the structure along path 1005, the clinician manipulates the sensor head until two shapes in image 1130 (FIG. 11), one from each array, coincide with one another. The shapes correspond to the structure. Once the shapes coincide, the clinician assumes that the structure is aligned along path 1005.

Second, the clinician uses the depth scale to determine the depth of the center of the structure. The clinician selects a point on the displayed images which corresponds to the sensor that lies on a line drawn perpendicular to the surface of one of the arrays from the center of the structure. The point on the image is typically a center of the superimposed shapes image 1130, or a center of one of the shapes in images 1105 and 1110 (all in FIG. 11).

We will now describe in detail these two tasks. First, the clinician centers the structure along path 1005. Each array of device 700 can be said to have a "field of vision." This field of vision is generally the area directly underlying each array, defined by perpendicular lines extending from the borders of each array, e.g. in FIG. 10, lines 1050. The area enclosed within these lines is the field of vision of device 700. The smaller the extension angle θ is, the larger the field of vision of device 700.

Therefore, at the beginning of the biopsy procedure when the clinician is interested in locating the structure, the clinician opens extensions 715, 720 so that device 700 has the largest possible field of vision. The clinician, for example, may set pivot angle θ to zero. The clinician then examines the breast to locate the structure selected for biopsy. The clinician may then confirm the diagnosis in the same manner as with device 100.

Once the clinician has found the structure on which biopsy is to be performed, the clinician centers and constrains the underlying structure along path 1005 (FIG. 10). The clinician closes the extensions somewhat. As the pivot angle θ increases, the extensions further constrain the underlying structure from moving from side to side.

Figure 12:
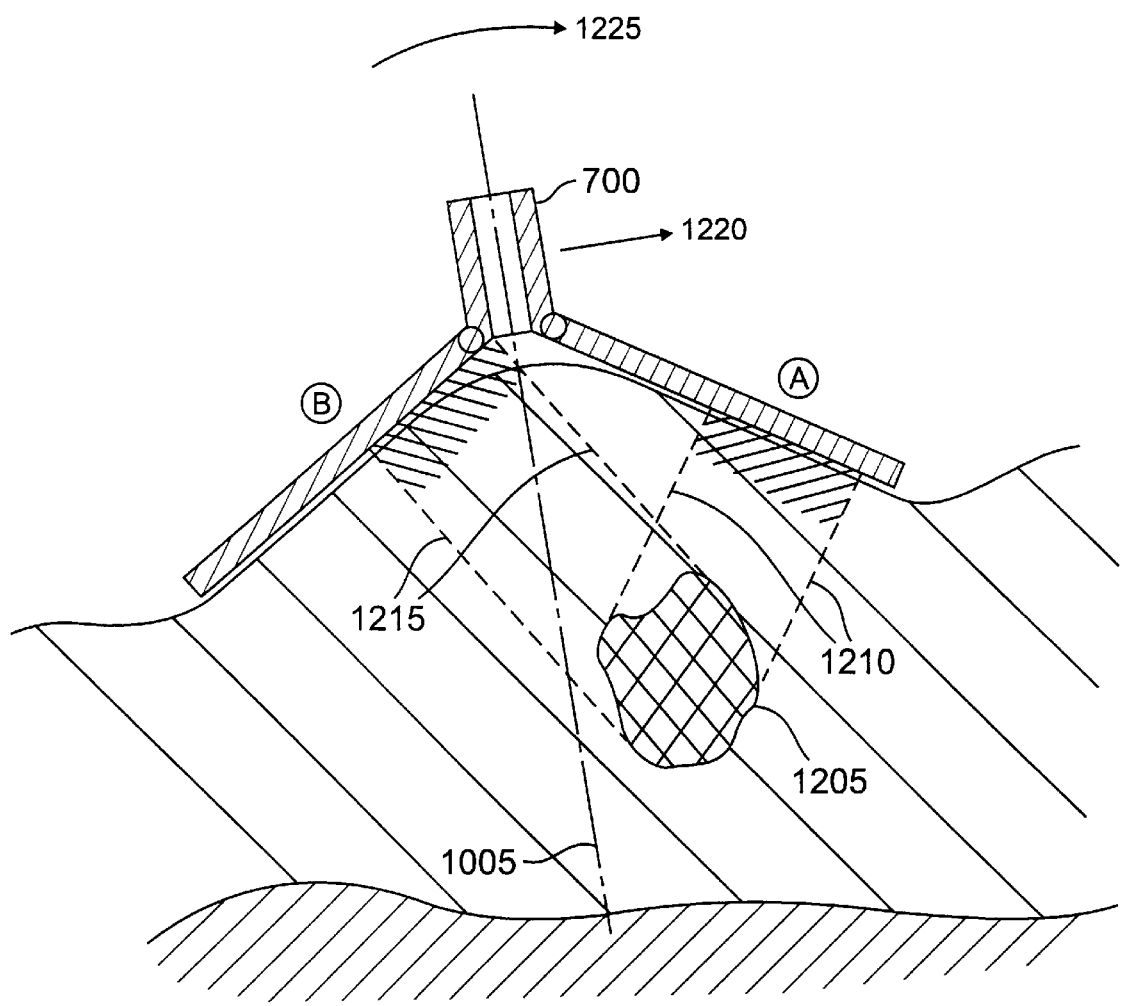
Figure 13:
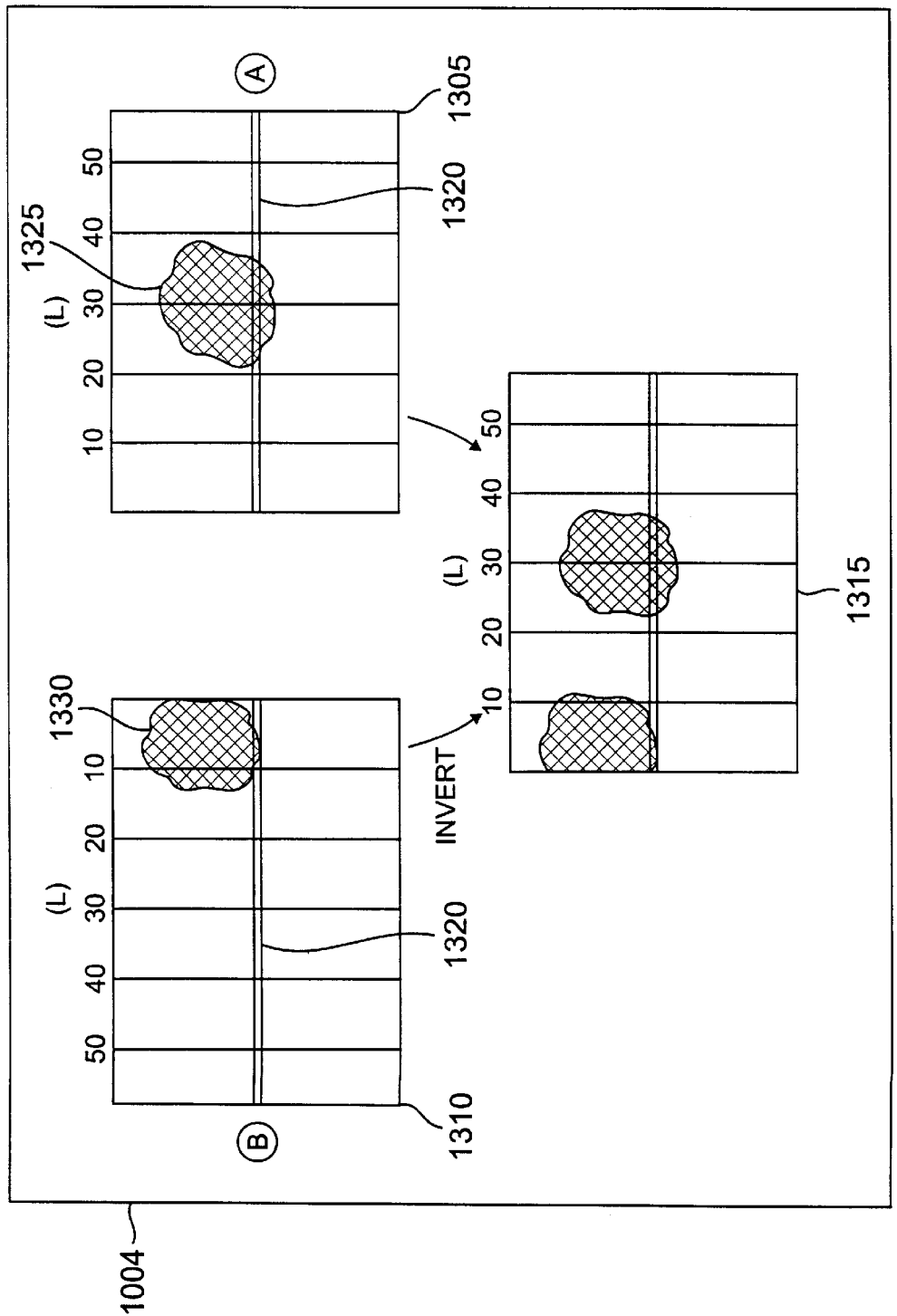

FIG. 12 illustrates a situation where an underlying structure 1205 is not centered along path 1005. Underlying structure 1205 generally primarily exerts pressure on arrays 705 and 710 within the area defined by a set of lines 1210 and another set of lines 1215. The lines in each set 1210, 1215 are parallel to each other, extend from the outer most edges of structure 1205, and are perpendicular to the surface of the array. As is readily apparent, the locations of the imposed pressure on the two arrays are not symmetrical. FIG. 13 illustrates the corresponding asymmetry between the positions of shapes 1325, 1330 relative to corresponding images 1305, 1310. (Images 1305, 1310 respectively represent the signals from arrays 705, 710.) This asymmetry indicates that the center of the structure is not aligned with the cannula. Similarly image 1315, which shows images 1305 and 1310 superimposed on one another as described above, shows the two shapes as separate. This would not be the case if the structure was centered along the path 1005, as seen in FIGS. 10 and 11.

To align the center of the structure with the cannula and path 1005, the clinician manipulates the sensor head, for example, by tilting, pivoting, or rotating the sensor head, until the two shapes in image 1315 in FIG. 13 substantially coincide (as in image 1130 in FIG. 11). Generally, to correctly target a structure the user must adjust the tilting angle of the sensor head and translate the sensor head along the surface of the tissue. In the case of the situation in FIG. 12, for example, the clinician may translate the device in a direction 1220 while tilting or rotating the sensor head in a direction 1225 to center structure 1205.

When the clinician has centered the underlying structure along path 1005 under cannula 745, the clinician then closes the extensions as far as is practicable. This has two desired results. First, the larger the angle θ between the extensions and plate 740 is, the better the underlying structure is constrained by the extensions. Second, the larger the angle θ is, the smaller the field of view of the arrays, and therefore the more accurate the reading obtained from the depth scale.

Having described how the clinician centers the structure along path 1005, we will now describe the second task a clinician performs to determine the depth of the center of the structure, i.e. selecting a point on the image that represents the sensor that would have obtained the pressure readings from the array from the center of the structure. Typically, structures on which biopsies are performed have substantially spherical shapes. Therefore, their pressure signatures on the arrays have a generally circular outline, and appear as substantially circular shapes in the displayed top view of the three dimensional images, as in images 1305 and 1310 in FIG. 13. Since the pressure on the arrays is exerted perpendicularly to the array, the center of the circular image would correspond to the center of the spherical structure. Therefore, once the clinician has determined the center of the displayed image, the clinician has in essence also determined the point in the image that corresponds to the sensor that would have been pressed by the center of the structure. The clinician can thus determine the depth of the center by reading a value on the depth scale corresponding to the determined center of the shape. In other words, when the images are aligned, the user knows that the center of the structure is beneath the cannula on line 1005, and that the depth reading associated with the center of a displayed image corresponds to the depth of the center of the structure.

Referring to back to FIG. 10, once the desired depth value is known, the clinician positions a sliding stop 1015 a distance L from the tip of the needle, where L equals the determined depth value (see equation 2). The clinician then secures sliding stop 1015 using a screw 1017 (FIG. 10). The clinician then inserts biopsy needle 755 into cannula 745 to perform the biopsy. The cannula 745 will guide biopsy needle 1010 along path 1005 towards the center of structure 1030. Needle 755 is inserted through cannula 745 during the biopsy until sliding stop 1015 then abuts the top of the cannula 745. At this point, the clinician knows with some certainty that the tip of needle 755 has reached the desired depth and will obtain a proper sample from the center of the underlying structure. As in the first embodiment, the clinician can confirm this by viewing the real time image on display 216.

In an alternative embodiment of device 700, the sensor head can be constructed to have more than two arrays, for example, three or more arrays spaced equally around the cannula. This multi-array embodiment would better constrain the structure.

The sensor heads in the above described devices may be directly applied to the surface of the tissue to be examined, or the surface of the sensors or the tissue to be examined may be coated with a lubricant, such as a gel. The lubricant helps the sensors glide easily over the tissue surface and improves the mechanical coupling between the tissue and the sensors.

Yet other embodiments are also within the scope of the following claims.

What is claimed is:

1. A device comprising
   a first member and a second member each of which is configured to be pressed against tissue,
   a first plurality of sensors and a second plurality of sensors respectively disposed on said first member and said second member for generating signals in response to pressure imposed thereon by underlying tissue when said the respective member is pressed against the tissue for detection of an underlying tissue structure in the tissue, and
   a locating device, coupled to said first member and said second member at a selected position with respect to said first plurality of sensors and said plurality of sensors, for indicating a location of the structure based on the signals generated by said first plurality of sensors and said second plurality of sensors, said locating device being an instrument guide for use with an instrument for diagnosing or treating the underlying tissue structure.

2. The device of claim 1 wherein said instrument guide is configured to be used with a medical instrument comprising at least one of a group comprising surgical instruments, laser fibers, RF electrodes, cryogenic probes, and devices for implanting materials in the underlying tissue structure, wherein said material comprises at least one of a group comprising radioisotopes, drugs, biologic agents, and alcohol.

3. The device of claim 1 further comprising a lubricant disposed between the each said plurality of sensors and the tissue.

4. The device of claim 1 wherein said instrument guide comprises a biopsy instrument guide.

5. The device of claim 1 wherein said guide includes a cannula mounted to said members at the selected position and having a passage sized to receive an instrument for diagnosing or treating the underlying tissue structure.

6. The device of claim 5 wherein said first plurality of sensors and said second plurality of sensors are respectively disposed on a lower surface of said first member and said second member, said cannula being attached to said members so that said passage is arranged at the selected position.

7. The device of claim 6 wherein said first plurality of sensors and said second plurality of sensors are arranged in arrays, and said passage is arranged between said arrays.

8. The device of claim 1 further comprising
 a processor for generating an image of the underlying tissue structure based on said signals, and
 a display device for displaying said image.

9. The device of claim 8 wherein said processor is configured to produce an indicator of said selected position of the locating device relative to the image of the underlying tissue structure for display on said display device with said image.

10. The device of claim 9 wherein said processor is further configured to cause said indicator to be substantially aligned with a portion of said image on said display device if a corresponding portion of the underlying tissue structure is positioned beneath said instrument guide.

11. The device of claim 1 wherein said guide includes a cannula mounted between the first member and said second member at the selected position, said cannula having a passage sized to receive an instrument for diagnosing or treating the underlying tissue structure.

12. The device of claim 11 further comprising
 a processor for generating a first image of the underlying tissue structure based on said signals produced by the first sensors, and generating a second image of the underlying tissue structure based on said signals produced by the second sensors, and
 a display device for displaying said first image and said second image.

13. The device of claim 12 wherein said processor is configured to cause said first image and said second image to be displayed on said display device in a manner that indicates a location of the underlying tissue structure relative to said instrument guide.

14. The device of claim 13 wherein said processor is further configured to cause said first image and said second image to be substantially aligned with each other on said display device if the underlying tissue structure is positioned beneath said instrument guide.

15. The device of claim 1 wherein the first member and said second member are pivotally mounted with respect to said instrument guide to allow said members to be pivoted with respect to each other so that an underlying tissue structure is disposed beneath and between said members, and further comprising
 a measurement device for determining a pivot angle of one of said members,
 said processor being configured to determine a depth of the underlying tissue structure beneath a surface of the tissue based on said angle and said signals generated by the first plurality of sensors and said second plurality of sensors.

16. The device of claim 15 wherein said processor is further configured to cause an indication of the depth of the underlying tissue structure to be displayed on a display device.

17. The device of claim 15 wherein said instrument guide includes a cannula having a selected length passage sized to receive an instrument for diagnosing or treating the underlying tissue structure, and further comprising an instrument for diagnosing or treating the underlying tissue structure having an adjustable length, thereby to allow a user to set the length of said instrument to the selected length of the cannula passage plus the depth of the underlying tissue structure determined by said processor.

18. A method comprising
 providing a device that includes: (1) a first member and a second member having a first plurality of sensors and a second plurality of sensors respectively disposed thereon for generating signals in response to pressure imposed thereon by underlying tissue when said first member and said second member are pressed against the tissue for detection of an underlying tissue structure in the tissue, and (2) a locating device, coupled to said first member and said second member at a selected position with respect to said first plurality of sensors and said second plurality of sensors, for indicating a location of the structure based on the signals generated by said first plurality of sensors and said second plurality of sensors, said locating device being an instrument guide for use with an instrument for diagnosing or treating the underlying tissue structure,
 pressing said first member and said second member against the tissue, and
 positioning said locating device relative to an underlying tissue structure based on the signals generated by said first plurality of sensors and said second plurality of sensors.

19. The method of claim 18 wherein said instrument guide is configured to be used with a medical instrument comprising at least one of a group comprising biopsy instruments, surgical instruments, laser fibers, RF electrodes, cryogenic probes, and devices for implanting materials in the underlying tissue structure, wherein said material comprises at least one of a group comprising radioisotopes, drugs, biologic agents, and alcohol, and the method further comprising
 using said instrument guide to direct said medical instrument to the underlying tissue structure to treat or diagnose the underlying tissue structure.

20. The method of claim 18 further comprising:
 using a lubricant between the each said plurality of sensors and the tissue.

21. The device of claim 18 wherein said instrument guide comprises a biopsy instrument guide.

22. The method of claim 18 further comprising generating an image of an underlying tissue structure based on said signals, displaying said image on a display device, and performing said positioning step based on a position of the image on the display device.

23. The method of claim 22 further comprising displaying an indicator of said selected position of the locating device relative to the image of the underlying tissue structure on said display device with said image, and performing said positioning step by manipulating said member first member and said second on the tissue to produce relative movement between said indicator and said image on said display device until said indicator is substantially aligned with a portion of said image on said display device, thereby indicating that a corresponding portion of the underlying tissue structure is positioned beneath said instrument guide.

24. The method of claim 23 wherein said first plurality of sensors and said second plurality of sensors are respectively disposed on a lower surface of said first member and said second member, said guide including a cannula attached to said members so that a passage of said cannula is arranged at the selected position, said indicator indicating a position of said passage, and further comprising inserting the instrument for diagnosing or treating the underlying tissue structure through said cannula passage to diagnose or treat the underlying tissue structure when said indicator is substantially aligned with a portion of said image on said display device.

25. The method of claim 18 further comprising generating a first image of the underlying tissue structure based on said signals produced by the first plurality of sensors, and generating a second image of the underlying tissue structure based on said signals produced by the second plurality of sensors, displaying said first image and said second image on a display device, and performing the positioning step based on relative positions of said first image and said second image on the display device.

26. The method of claim 25 further comprising manipulating said device on the tissue to cause said first image and said second image to move with respect to each other on said display device until portions of said images are substantially aligned on said display device, thereby indicating that a corresponding portion of the underlying tissue structure is positioned beneath said instrument guide, and using said guide to direct an instrument for diagnosing or treating the underlying tissue structure to the corresponding portion of the underlying tissue structure.

27. The method of claim 18 further comprising determining a depth of the underlying tissue structure based on said signals produced by the first plurality sensors and said signals produced by the second plurality of sensors.

28. The method of claim 27 further comprising displaying an indication of the depth of the underlying tissue structure on said display device.

29. The method of claim 18 wherein the instrument guide includes a cannula and said first member and said second member are pivotally mounted with respect to said cannula, and further comprising pivoting said members with respect to each other so that the underlying tissue structure is disposed beneath and between said members, determining a pivot angle of one of said members, and determining a depth of the underlying tissue structure beneath a surface of the tissue based on said angle and said signals generated by the first plurality of sensors and said second plurality of sensors.

30. The method of claim 29 wherein said cannula has a selected length passage sized to receive an instrument for diagnosing or treating the underlying tissue structure, and further comprising providing an instrument for diagnosing or treating the underlying tissue structure, the instrument having an adjustable length, and adjusting the length of the instrument to the selected length of the cannula passage plus the determined depth of the underlying tissue structure.

* * * * *